US009625583B2

(12) United States Patent
Beddar et al.

(10) Patent No.: US 9,625,583 B2
(45) Date of Patent: Apr. 18, 2017

(54) LARGE-VOLUME SCINTILLATOR DETECTOR FOR RAPID REAL-TIME 3-D DOSE IMAGING OF ADVANCED RADIATION THERAPY MODALITIES

(71) Applicants: Board of Regents, The University of Texas System, Austin, TX (US); Université Laval, Quebec (CA)

(72) Inventors: A. Sam Beddar, Houston, TX (US); Louis Archambault, Quebec (CA); Daniel Robertson, Houston, TX (US)

(73) Assignees: Board of Regents, The University of Texas System, Austin, TX (US); Université Laval, Quebec (CA)

( * ) Notice: Subject to any disclaimer, the term of this patent is extended or adjusted under 35 U.S.C. 154(b) by 0 days.

(21) Appl. No.: 14/893,872

(22) PCT Filed: May 30, 2014

(86) PCT No.: PCT/US2014/040228
§ 371 (c)(1),
(2) Date: Nov. 24, 2015

(87) PCT Pub. No.: WO2014/194194
PCT Pub. Date: Dec. 4, 2014

(65) Prior Publication Data
US 2016/0103227 A1      Apr. 14, 2016

Related U.S. Application Data

(60) Provisional application No. 61/829,397, filed on May 31, 2013.

(51) Int. Cl.
*G01T 1/00* (2006.01)
*G01T 1/29* (2006.01)
(Continued)

(52) U.S. Cl.
CPC ............. *G01T 1/10* (2013.01); *A61N 5/1071* (2013.01); *G01T 1/2042* (2013.01); *G01T 1/29* (2013.01)

(58) Field of Classification Search
CPC ....... A61N 5/1071; G01T 1/10; G01T 1/2042; G01T 1/29
See application file for complete search history.

(56) References Cited

U.S. PATENT DOCUMENTS 5,245,191 A * 9/1993 Barber .................. G01T 1/2928
250/363.04
5,265,475 A    11/1993 Messinger et al.
(Continued)

FOREIGN PATENT DOCUMENTS

| WO | WO 00/79302 | 12/2000 | |
| WO | WO 2012/159201 | 11/2012 | |
| WO | WO 2012159201 A1 * | 11/2012 | ............. G01T 1/161 |

OTHER PUBLICATIONS

Archambault et al., "Measurement accuracy and Cerenkov removal for high performance, high spatial resolution scintillation dosimetry," Med. Phys., 33(1):128-135, 2006.
(Continued)

*Primary Examiner* — Mark R Gaworecki
(74) *Attorney, Agent, or Firm* — Parker Highlander PLLC

(57) ABSTRACT

An apparatus and method for measuring three-dimensional radiation dose distributions with high spatial and temporal resolution using a large-volume scintillator. The scintillator converts the radiation dose distribution into a visible light distribution. The visible light is transported to one or more photo-detectors, which measure the light intensity. The light signals are processed to correct for optical artifacts, and the three-dimensional light distribution is reconstructed. The reconstructed light distribution is post-processed to convert light amplitudes to measured radiation doses. The high
(Continued)

temporal resolution of the detector makes it possible to observe the evolution of a dynamic dose distribution as it changes over time. Integral dose distributions can be measured by summing the dose over time.

20 Claims, 6 Drawing Sheets

(51) Int. Cl.
| | | |
|---|---|---|
| *G01T 1/20* | | (2006.01) |
| *A61N 5/10* | | (2006.01) |
| *G01T 1/10* | | (2006.01) |
| *G01T 1/204* | | (2006.01) |

(56) References Cited

U.S. PATENT DOCUMENTS

| | | | |
|---|---|---|---|
| 5,856,673 A | 1/1999 | Ikegami et al. | |
| 5,905,263 A | 5/1999 | Nishizawa et al. | |
| 6,066,851 A | 5/2000 | Madono et al. | |
| 6,087,666 A | 7/2000 | Huston et al. | |
| 6,125,335 A | 9/2000 | Simon et al. | |
| 6,151,769 A | 11/2000 | Bliss et al. | |
| 6,255,659 B1 * | 7/2001 | Sandison | G01J 1/50 250/338.1 |
| 7,154,097 B2 | 12/2006 | Fontbonne et al. | |
| 7,432,510 B2 | 10/2008 | Yeo | |
| 7,456,405 B1 * | 11/2008 | Iwatschenko-Borho | G01T 1/023 250/339.02 |
| 7,636,419 B1 * | 12/2009 | Nelson | A61N 5/1048 250/363.01 |
| 7,662,083 B2 | 2/2010 | Gueye et al. | |
| 7,804,075 B2 | 9/2010 | Ntziachristos et al. | |
| 8,133,167 B2 | 3/2012 | Gueye et al. | |
| 8,183,534 B2 | 5/2012 | Lacroix et al. | |
| 9,028,390 B2 | 5/2015 | Keppel et al. | |
| 2001/0047136 A1 | 11/2001 | Domanik et al. | |
| 2002/0070365 A1 | 6/2002 | Karellas | |
| 2002/0125412 A1 | 9/2002 | Barnett | |
| 2004/0174951 A1 | 9/2004 | Hoffman | |
| 2005/0123089 A1 * | 6/2005 | Man | A61B 6/00 378/4 |
| 2005/0151071 A1 | 7/2005 | Nilsson | |
| 2005/0195318 A1 | 9/2005 | Komatsu | |
| 2006/0017009 A1 | 1/2006 | Rink et al. | |
| 2006/0027756 A1 | 2/2006 | Thomson et al. | |
| 2006/0054828 A1 | 3/2006 | Fritzler et al. | |
| 2006/0169917 A1 | 8/2006 | Franz | |
| 2007/0057164 A1 | 3/2007 | Vaughnn et al. | |
| 2007/0129593 A1 | 6/2007 | Gueye et al. | |
| 2008/0073568 A1 | 3/2008 | Yamazaki et al. | |
| 2008/0169421 A1 | 7/2008 | Danielsson | |
| 2008/0187095 A1 * | 8/2008 | Boone | A61B 6/0435 378/37 |
| 2008/0272310 A1 | 11/2008 | Khalil | |
| 2009/0003512 A1 * | 1/2009 | Pouliot | A61B 6/466 378/4 |
| 2009/0014665 A1 | 1/2009 | Fleming et al. | |
| 2009/0236510 A1 | 9/2009 | Lacroix et al. | |
| 2009/0283682 A1 | 11/2009 | Star-Lack et al. | |
| 2009/0294687 A1 | 12/2009 | Shofman et al. | |
| 2010/0001189 A1 | 1/2010 | Federici | |
| 2010/0140484 A1 | 6/2010 | Snoeren et al. | |
| 2011/0092814 A1 * | 4/2011 | Yamaya | A61N 5/1048 600/427 |
| 2011/0157387 A1 * | 6/2011 | Han | H04N 5/2253 348/218.1 |
| 2012/0068075 A1 | 3/2012 | Beddar et al. | |
| 2012/0168630 A1 | 7/2012 | Beddar et al. | |

OTHER PUBLICATIONS

Archambault et al., "Plastic scintillation dosimetry: optimal selection of scintillating fibers and scintillators," *Med. Phys.*, 32(7):2271-2278, 2005.

Beddar et al., "A miniature "scintillator-fiberoptic-PMT" detector system for the dosimetry of small fields in stereotactic radiosurgery," *IEEE Transactions on Nuclear Science*, 48(3):924-928, 2001.

Beddar et al., "Cerenkov light generated in optical fibres and other light pipes irradiated by electron beams," *Phys. Med. Biol.*, 37(4):925-935, 1992.

Beddar et al., "Plastic scintillation dosimetry for radiation therapy: minimizing capture of Cerenkov radiation noise," *Phys. Med. Biol.*, 49:783-790, 2004.

Beddar et al., "Plastic scintillation dosimetry: optimization of light collection efficiency," *Phys. Med. Biol.*, 48:1141-1152, 2003.

Beddar et al., "Water-equivalent plastic scintillation detectors for high-energy beam dosimetry: I. physical characteristics and theoretical considerations," *Phys. Med. Biol.*, 37(10):1883-1900, 1992.

Beddar et al., "Water-equivalent plastic scintillation detectors for high-energy beam dosimetry: II. Properties and measurements," *Phys. Med. Biol.*, 37(10):1901-1913, 1992.

Das et al., "Characteristics of a scintillator-based daily quality assurance device for radiation oncology beams," *Med. Phys.*, 23(12):2061-2067, 1996.

De Boer, "Optical filtering and spectral measurements of radiation-induced light in plastic scintillation dosimetry," *Phys. Med. Biol.*, 38:945-958, 1993.

Essers and Mijnheer, "In Vivo dosimetry during external photon beam radiotherapy," *Int. J. Radiation Oncology Biol. Phys.*, 43(2):245-259, 1999.

Fiorino et al., "Quality assurance by systematic in vivo dosimetry: results on a large cohort of patients," *Radiotherapy and Oncology*, 56:85-95, 2000.

Ikhlef et al., "X-ray imaging and detection using plastic scintillating fibers," *Nuclear Instruments and Methods in Physics Research A.*, 442:428-432, 2000.

Jordan, "Evaluation of ruby as a fluorescent sensor for optical fiber-based radiation dosimetry," *SPIE*, 2705:170-178, 1996.

Létourneau et al., "Miniature scintillating detector for small field radiation therapy," *Med. Phys.*, 26(12):2555-2561, 1999.

Macri et al., "Readout of scintillating plastic fibers with an APD array and prototype ASIC," *IEEE Transactions on Nuclear Science*, 50(4):928-935, 2003.

PCT International Search Report and Written Opinion issued in International Application No. PCT/US2014/040228, mailed Oct. 16, 2014.

* cited by examiner

LARGE-VOLUME SCINTILLATOR DETECTOR FOR RAPID REAL-TIME 3-D DOSE IMAGING OF ADVANCED RADIATION THERAPY MODALITIES

CROSS-REFERENCE TO RELATED APPLICATIONS

This application is a national phase application under 35 U.S.C. §371 of International Application No. PCT/US2014/040228, filed May 30, 2014, which claims priority to U.S. Provisional Patent Application Ser. No. 61/829,397, filed May 31, 2013, the contents of each of which are incorporated by reference herein.

BACKGROUND OF THE INVENTION

Certain embodiments of the present invention relate to the field of radiation therapy and radiation dose measurement for all types of external ionizing radiation, including photons, proton beams, heavy ion beams, and for internally-administered radioactive isotopes and x-ray sources.

The properties of plastic and organic scintillators are known to be ideal for radiation dosimeters used in radiation therapy. A series of seminal papers published in the early 90s have established that plastic scintillation detectors have a unique set of advantages such as water-equivalence, dose linearity, dose rate independence and energy independence under irradiation by megavoltage photon and electron beams. These scintillators can therefore be used for precise and accurate measurements of radiation doses involved in radiation therapy treatments. The ideal characteristics of plastic scintillators first prompted their use as small, single-point dose detectors, and then as arrays in large detector systems. Two-dimensional systems have also been proposed by using continuous sheets of scintillating material.

Fast and accurate measurement of radiation doses in multiple points or in a plane is useful, but as the capacity for conformal radiation beam delivery increases, one is confronted with complex dose patterns following the shape of a tumor in three dimensions. Furthermore, such complex dose patterns are often delivered dynamically either with rotational treatment modalities such as volumetric-modulated arc therapy (VMAT) or intensity modulated proton therapy (IMPT) delivered with scanned pencil beams. Such treatment modalities are among the fastest growing approaches for delivering highly conformal doses of radiation with curative intent.

A fast, three-dimensional dose detector would allow a complete mapping of the radiation dose no matter how complex. At the present time, only dosimetric gels can be used to make thorough 3D dose measurements. Dosimetric gels are either based on the behavior of ferrous ions or on the polymerization of a monomer in response to irradiation. A large variety of chemical formulas are available for the gels, and each has its own set of advantages and disadvantages. However, they usually share a delicate fabrication process; they require time-consuming post-processing manipulation and analysis; and they may suffer from various artifacts. These characteristics make the daily clinical usage of dosimetric gels somewhat challenging. In addition, dosimetric gels measure only the integral dose from an entire treatment delivery. They are not capable of measuring the time-dependent aspects of dose delivery.

Aside from dosimetric gels, arrays of radiation dose detectors (ionization chambers or diodes) have been developed to partially map complex dose distributions. However, for an accurate measurement of a three-dimensional dose distribution, the detector itself must not alter the passage of ionizing radiation. For radiation therapy applications, we are interested in the interaction between ionizing radiation and materials similar to water and/or human tissues. The use of detector arrays is therefore not ideal because such detectors are either based on silicon diodes or air-filled ionization chambers, both of which significantly differ from water and human tissues. Consequently detector arrays cause perturbations of the radiation fields. For this reason, most detector arrays are solely used to monitor radiation in the plane perpendicular to the radiation beam. Furthermore, detector arrays often suffer from intrinsic limitations. The size of the detector elements might limit the spatial resolution of the measurements (e.g. the ionization chambers used in arrays often have a detector size of more than 5 mm). The minimum possible spacing between detectors might also create gaps where no information can be obtained.

Because of the inherent water equivalence of plastic scintillators, a detector made of this material is similar to water and human tissue and does not perturb an incident radiation beam as it travels through the device. A scintillator-based prototype for measuring 3D doses produced by eye-plaque brachytherapy applicators has been reported. This prototype performs a tomographic reconstruction of the dose by rotating a vial of liquid scintillator containing the eye plaque. This prototype was designed only for measuring dose distributions of small volumes (<20 cm3) and required long acquisition times (more than 5 hours for 64 projection angles). However, this work proves that scintillator based system can be used for 3D dose measurements.

Recently, a volumetric dose detector based on liquid organic scintillator was developed. This liquid scintillator (LS) detector device is imaged by a charge-coupled device (CCD) camera. A radiation beam incident on the LS produces a pattern of scintillation light. This pattern is a function of the amount of radiation dose deposited. The CCD camera placed at one side of the cubic LS volume captures images of this light distribution. The LS detector system is not a 3-D dosimeter per se because the CCD images represent the integral of all the light produced in the volume along the camera axis. Even if the images contain information about the entire 3-D dose distribution, it is impossible to extract the dose delivered at a given point. The LS detector system was developed for two main applications: one for proton therapy and one for intensity modulated radiation therapy (IMRT). For proton therapy the LS detector system was irradiated with passively scattered beams and magnetically scanned proton pencil beams. We have shown that with scanned proton beams, the lateral position and the depth (which is directly correlated to the energy of the protons) of individual beams can be measured with sub-millimeter accuracy. For IMRT the LS detector system was used as a verification device. Clinical treatment plans were transferred from the patient CT to the CT dataset of the LS detector. Then a forward projection of the planned dose was made to simulate the expected scintillation light distribution. Finally, the simulated and measured light distributions were compared for every segment of every beam to detect any discrepancies that could have occurred during the treatment.

SUMMARY OF THE INVENTION

Exemplary embodiments of the present disclosure may include a radiation dose detector device comprising a scintillating element, a plurality of light detectors configured to detect light emitted from the scintillating element, and a computer. In certain embodiments, the computer may be configured to receive data from the plurality of light detectors and configured to generate a three-dimensional map of light emitted from the scintillating element. In some embodiments, the plurality of light detectors may be configured to simultaneously detect light emitted from the scintillating element. In particular embodiments, at least one of the plurality of light detectors may be selected from the group consisting of: charge-coupled device (CCD) cameras, complementary metal-oxide sensor (CMOS) cameras, light field cameras, photodiode arrays and photomultiplier tube arrays.

In certain embodiments, the plurality of light detectors may be coupled to a housing. Particular embodiments may further comprise a collimator between the scintillating element and at least one of the plurality of light detectors. Some embodiments may also comprise one or more optical fibers between the scintillating element and at least one of the plurality of light detectors.

In certain embodiments, the computer may comprise a computer readable medium comprising software configured to execute a pre-processing algorithm, a tomographic reconstruction algorithm and a post-processing algorithm. In particular embodiments, the pre-processing algorithm may be configured to correct for both optical and dosimetric artifacts. In some embodiments, the tomographic reconstruction algorithm may convert data received from the plurality of light detectors into a three-dimensional dose distribution. In certain embodiments, the tomographic reconstruction algorithm may comprise a filtered backprojection algorithm. In particular embodiments, the tomographic reconstruction algorithm may comprise an iterative algorithm. In some embodiments, the post-processing algorithm may be configured to convert grayscale levels of three-dimensional light distribution into actual dose values by comparison with a reference measurement.

Certain embodiments of the present disclosure may include a three-dimensional radiation dose detector device comprising: a large continuous volumetric scintillating element; and means for measuring the light emission from the scintillating element from multiple positions or directions simultaneously and with high temporal resolution. In particular embodiments, the continuous volumetric scintillating element may have a volume of about 500 to 15,000 cubic centimeters, or more particularly 1,000 to 10,000 cubic centimeters, or still more particularly 3,000 to 7,000 cubic centimeters.

In certain embodiments, the radiation dose detector device may include means to correct for the varying response of scintillator yield when irradiated with particles of high linear energy transfer (LET). In certain embodiments, the radiation dose detector device may include a scintillating element comprised of a central or off-center embodiment to enclose any type of radioactive source.

In some embodiments, the temporal resolution may be up to 100 samples per second. In certain embodiments, the scintillating element may be an organic or inorganic material in solid, liquid, or gelatinous state. In particular embodiments, the means for measuring light emission may comprise one or more charge-coupled devices, complementary metal-oxide-semiconductor devices, light field cameras, photomultiplier tubes, photodiodes, avalanche photodiodes, or other devices capable of light detection.

In some embodiments, the means of measuring light emission may comprise one or more light-field imagers or plenoptic cameras. In particular embodiments, the means for measuring light emission may include detectors equally spaced at an angle θ, with the sum of all angles equal to 360 degrees. In certain embodiments, the means for measuring light emission may include detectors unequally-spaced at angles θi, where the sum of all θi equals 360 degrees or less. In particular embodiments, the means for measuring light emission may include detectors in non-planar distributions, including spherical, cubic, and other three-dimensional detector distributions. In some embodiments, the volumetric scintillating element may be formed in the shape of a cube, cylinder, sphere, ellipsoid, prism, or other geometric shape. In certain embodiments, the volumetric scintillating element may be formed in a shape similar to one or more parts of a human body.

In particular embodiments, the volumetric scintillating element may be encased in a body that is transparent to the scintillation light. In some embodiments, the transparent encasing body may be formed in a cube, cylinder, sphere, ellipsoid, prism, or other geometric shape. In particular embodiments, the transparent encasing body may be formed in a shape similar to one or more parts of a human body.

In some embodiments, the surface of said volumetric scintillating element may be treated to prevent light reflection at the interface between said volumetric scintillating element and any adjacent components or the surrounding medium. Particular embodiments may further include a light-guiding apparatus which directs light from the volumetric scintillating element to said means for measuring light emission. In some embodiments, the light-guiding apparatus may include fiber optics with low numerical aperture. In certain embodiments, the light-guiding apparatus may include lenses and/or mirrors.

In particular embodiments, the light-guiding apparatus may include gaps at one or more angles whereby radiation from an external source may enter the volumetric scintillating detector without passing through the light-guiding apparatus. Some embodiments may include a collimator grid between said volumetric scintillating element and said means for measuring light emission.

In certain embodiments, the collimator grid may include gaps at one or more angles whereby radiation from an external source may enter the volumetric scintillating detector without passing through the collimator grid. In particular embodiments, the measurement of light emission may be performed with high temporal resolution. In some embodiments, the temporal resolution may be up to 100 samples per second.

In certain embodiments, the means for measuring the light emission may be activated and/or deactivated by a signal from a radiation generating device or a radiation source control or monitoring mechanism. In particular embodiments, the measurement of light emission may be integrated over a complete treatment fraction. Some embodiments may further include means for the correction of optical artifacts introduced by the passage of scintillation light through any components of said radiation dose detector, including but not limited to reflection, refraction, photon scattering, light attenuation, vignetting, collimator obstruction, and lens aberration.

Certain embodiments of the present disclosure may include a methodology to correct for optical artifacts occurring in the propagation of light within a radiation dose detector device as previously described (e.g. a three-dimensional radiation dose detector device comprising a large continuous volumetric scintillating element, and means for measuring the light emission from said scintillating element from multiple positions or directions simultaneously and with high temporal resolution.) In particular embodiments, the methodology may correct artifacts including but not limited to reflection, refraction, photon scattering, light attenuation, vignetting, collimator obstruction, and lens aberration.

Certain embodiments of the present disclosure may include a methodology to correct for the varying response of scintillator yield when irradiated with particles of high linear energy transfer (LET). Particular embodiments of the present disclosure may include a methodology to remove or quantify the light produced by Cerenkov radiation within a radiation dose detector device as previously described (e.g. a three-dimensional radiation dose detector device comprising a large continuous volumetric scintillating element, and means for measuring the light emission from said scintillating element from multiple positions or directions simultaneously and with high temporal resolution.) Some embodiments of the present disclosure may include a methodology to produce a sinogram by interpolating data acquired by arrays of photodetectors with a radiation dose detector device as previously described. Certain embodiments of the present disclosure may include a dose reconstruction methodology to convert the sinogram into a three-dimensional dose map using filtered backprojection. Particular embodiments may include a methodology to convert the sinogram into a three-dimensional dose map using iterative reconstruction algorithms.

Specific embodiments may include a methodology to calibrate the radiation dose detector device as previously described (e.g. a three-dimensional radiation dose detector device comprising a large continuous volumetric scintillating element, and means for measuring the light emission from said scintillating element from multiple positions or directions simultaneously and with high temporal resolution) using one or more irradiations of known dose.

47. The radiation dose detector device of claim 13, wherein the scintillating element is comprised of a central or off-center embodiment to enclose any type of radioactive source.

In the following, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

Certain embodiments of the present invention aim to provide a three-dimensional dose detector system that can measure the three-dimensional radiation dose delivered by any type of external beam radiation therapy machine such as, but not restricted to, linear accelerators, cobalt-60 based devices, and accelerators for protons and other heavy ions. The detector can also measure the three-dimensional radiation dose delivered by radionuclide sources. Embodiments of the present invention can provide a methodology to collect the dosimetric signal in real time or near-real time with high temporal resolution, as well as a way to reconstruct a quantitative three-dimensional dose distribution from this signal. The dosimetric information thus reconstructed will be continuous (i.e. no gaps) and will possess a high spatial resolution.

In the present invention, a radiation detector system capable of measuring complex radiation dose distributions in three dimensions in real time or near-real time is provided. The detector system comprises a continuous (i.e. non-segmented) water-equivalent scintillator volume, a light guiding apparatus, a data acquisition method, and a dose reconstruction method.

The continuous scintillator is the sensitive volume of the detector system. It comprises a scintillating element, which may be an organic or inorganic scintillator in liquid, gelatinous, or plastic form. Any of these materials are capable of converting energy deposited by ionizing radiation into visible light on a timescale of the order of the microsecond or less. In one embodiment the sensitive volume is located inside an encasing body of a material transparent to the light emitted by the scintillator. The encasing body may have several possible shapes including but not limited to a cylinder, an elliptic cylinder, a cube, or a shape emulating a human body. The purpose of this encasing body is to attenuate ionizing radiation while allowing the passage of scintillation light. In one embodiment the surface of the encasing body is coated to prevent reflection of light at the interfaces between the encasing body and the scintillating element or the air surrounding the detector.

The light guiding apparatus comprises a system to collect the light escaping from the scintillator detector in order to direct it toward the photodetector. Collection is made at multiple angles around the scintillator volume and multiple positions for each given angle. In one embodiment the whole scintillator volume is surrounded by a collecting apparatus, while in another embodiment a gap is present in the collecting apparatus to allow irradiation of the sensitive volume with external beams of radiation at multiple angles. The light guiding and collection element can include one or more of the following: bundles of optical fiber with low numerical aperture, mirrors, optical lenses, and other forms of light pipes.

The data acquisition method comprises one or more light-sensing elements such as, but not limited to, CCD cameras, CMOS cameras, photodiode arrays or photomultiplier tube arrays. In one possible embodiment, a light-field imaging device is used in order to measure both the light and the direction of the light, hence acting as both the guiding apparatus and the data acquisition mechanism. In one embodiment a combination of different types of light-sensing elements is used to provide complementary information and facilitate the reconstruction process.

The dose reconstruction method comprises a pre-processing algorithm, a tomographic reconstruction algorithm, and a post-processing algorithm. The goal of the pre-processing algorithm is to correct for both optical and dosimetric artifacts. Examples of optical artifacts that can be corrected include, but are not limited to: light scattering, refraction, attenuation, and spurious light contamination. Dosimetric artifacts include quenching of the scintillation signal when irradiated by high-LET particles. The pre-processing algorithm may also interpolate the collected data in order to produce a sinogram. The tomographic reconstruction converts the collected data into a three-dimensional dose distribution. In one possible embodiment, the tomographic reconstruction is done with a filtered backprojection algorithm, while in another embodiment an iterative algorithm is used for the tomographic reconstruction. The spatial resolution can be determined by the user. The post-processing algorithm converts the grayscale levels of the three-dimensional dose distribution into actual dose values by comparison with a reference measurement. All dose reconstruction operations can be implemented on CPU or GPU.

DETAILED DESCRIPTION OF ILLUSTRATIVE EMBODIMENTS

Figure 1:
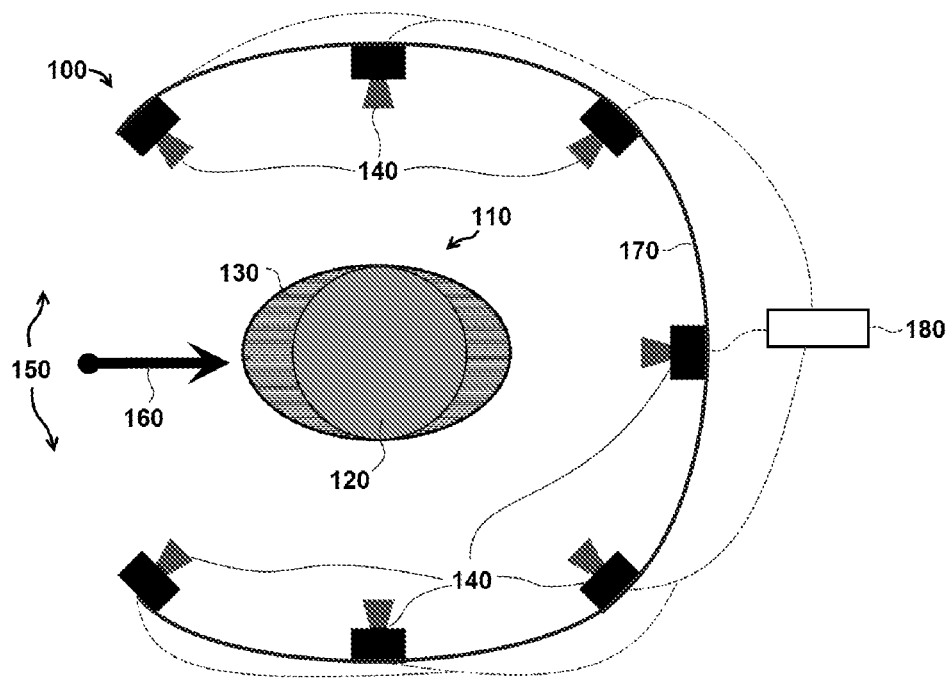
FIG. 1 shows a 3D detector system using a cylindrical plastic scintillator encased in an elliptic cylinder encasing body. Scintillation light is collected by arrays of CCD cameras. A gap in the ring of cameras is left to allow for delivery of the radiation beam.

FIG. 1 is a schematic of one exemplary embodiment of a three dimensional (3-D) radiation detector system 100 for measuring radiation dose distributions intended for cancer treatment. A cylindrical plastic scintillator assembly 110 comprises an active element 120 in detector system 100, and in certain embodiments, the dimensions of cylindrical plastic scintillator assembly 110 include a height of approximately 10 to 30 cm and a radius of approximately 5 to 15 cm. In particular embodiments, active element 120 is encased in an elliptic cylinder encasing body 130, which is also called a 'phantom' in the terminology of the medical physics community. In specific embodiments, the external dimensions of encasing body 130 are similar in size to a specific part of a human anatomy, including for example, a human head or human torso. In particular embodiments, encasing body 130 can be made of a clear plastic or other clear material with radiation absorption properties similar to those of water. In certain embodiments, the surface of encasing body 130 can be coated to reduce or prevent light reflection.

In the embodiment shown in FIG. 1, encasing body 130 is surrounded by a plurality of light detectors 140. In specific embodiments, light detectors 140 may comprise CCD cameras positioned at regular angles around the curved face of the elliptic cylinder volume. In the specific embodiment shown FIG. 1, seven cameras are shown at intervals of 45 degrees with one interval forming a gap 150 of 90 degrees. Gap 150 can be left in the regular spacing of light detectors 140 to allow a radiation beam to be delivered through the curved side of encasing body 130. In particular embodiments, light detectors 140 can be coupled to encasing body 130 by a housing 170 made of suitable material, e.g. metal or plastic. Housing 170 can rigidly maintain the positions of light detectors 140 while also blocking external light from entering the system. The distance between the surface of encasing body 130 and light detectors 140 can be between 20 cm and 50 cm in certain embodiments.

In specific embodiments, light detectors 140 may be CCD cameras that are fitted with low-distortion objective lenses. The lens settings can be selected such that the entire active element 120 is in the field of view of each camera, and the depth of field of each camera extends throughout the entire active element 120.

In particular embodiments, a collimator grid (not shown for purposes of clarity) may be included either at the surface of encasing body 130 or in the space between encasing body 130 and light detectors 140 (e.g. between encasing body 130 and an objective lens of each camera for embodiments utilizing cameras). This collimator grid can block light that is not parallel to the axis of a light detector 140, thereby reducing scattered light and decreasing optical artifacts in the detected images.

In exemplary embodiments, light detectors 140 may be configured as CCD cameras that are coupled to a computer 180 which controls the camera exposures and the data acquisition. In certain embodiments, the cameras may also be coupled to a signal provided by the radiation source to trigger the beginning and/or end of the image acquisition.

The embodiment of FIG. 1 may also comprise software implementing algorithms to convert images obtained from light detectors 140 into a three-dimensional (3-D) map of the light emission inside active element 120. Certain embodiments may use the Maximum-a-posteriori (MAP) iterative reconstruction algorithm to produce a 3-D reconstruction of the light emission inside active element 120. In particular embodiments, the algorithm can incorporate corrections for optical artifacts including attenuation and scattering of the scintillation light, refraction at material interfaces, and lens aberrations.

In particular embodiments, a post-processing algorithm can convert the grayscale levels of the three-dimensional dose distribution into actual dose values by comparison with a reference measurement. In the case of protons and other high-linear energy transfer (LET) radiation, a post-processing algorithm can include a method to correct for the non-linear scintillation response, or 'quenching,' of active element 120 when exposed to radiations of varying LET. This method was developed by Birks, and is described by the equation $$dS/dx = \frac{A \cdot dE/dx}{1 + kB \cdot dE/dx} \quad \text{(equation 1)}$$

where S is the scintillation light emitted, dE/dx is the energy deposited by the protons over a distance x in the medium, A is the scintillation efficiency of the medium, and k and B are empirical factors describing the non-scintillation energy loss in the medium. The A and kB factors can be determined by calibration and are unique for each scintillator material. The reconstruction and post-processing operations can be run on a computer with a multi-core processing unit.

The embodiment shown in FIG. 1 can be used to measure 3-D radiation dose distributions delivered by external beam radiation therapy equipment, including intensity-modulated photon beams and passive and scanned proton and heavy ion beams. The radiation beam can be delivered to detector 110 through gap 150 or, in specific embodiments, through flat faces of an elliptic cylinder-shaped encasing body 130. Encasing body 130 provides attenuation to radiation beam 160 in a manner similar to the tissues of a human body, so that the radiation dose measured in active element 120 is similar to the dose delivered to a similarly-located region inside a patient. The scintillator material can convert the radiation in the form of high-energy x-rays or particles into visible light, which is emitted isotropically from the location of energy deposition.

In certain exemplary embodiments, light emitted by active element 120 passes through encasing body 130 and reaches light detectors 140. In particular embodiments, the acquisitions of light detectors 140 are simultaneous and can be triggered manually or automatically through the software interface, or by signals from the radiation delivery machine.

Light detectors 140 may make one long acquisition to measure all of the light delivered by the radiation source, or they may rapidly acquire many images during the course of the radiation delivery. These acquisitions may be timed to align with times that the radiation is being delivered so that no (or minimal) signal is lost between camera frames in particular embodiments. In certain embodiments, the control software may also be used to send signals to cameras and the radiation delivery machine in order to trigger the radiation delivery and camera acquisition at the same time in a controlled manner.

In particular embodiments, the image data can be downloaded from light detectors 140 to the control computer, where it is processed by the 3-D reconstruction software to convert the images into a 3D map of the scintillation light intensity inside of active element 120. This software can use the maximum-a-posteriori (MAP) iterative reconstruction scheme using the one step late (OSL) algorithm to perform the reconstruction. The projection operators in the MAP algorithm include correction factors for light scattering, attenuation, noise, and refraction at material boundaries.

In certain embodiments, a post-processing algorithm uses a calibrated conversion factor to convert the reconstructed light signal into units of radiation dose to active element 120 of detector 110. In the case of irradiation by proton or heavy ion beams or other high-linear energy transfer (LET) radiation, the light distribution can be corrected for quenching, which is a non-linear response of scintillating materials to variations in the LET of the incident radiation. The quenching correction method can use equation 1 (provided above) with empirical factors provided by calibration measurements for the scintillating material. The term dE/dx can be obtained from Monte Carlo calculations of the specific proton or heavy ion beamline. These calculations provide a mapping of dE/dx to the beam energy and the depth in the material. This mapping can be used to assign the proper dE/dx value to each voxel in the reconstructed light distribution. After quenching correction is completed, the calibrated conversion factor can be applied to convert the corrected 3-D light distribution into a 3-D dose distribution.

Figure 2:
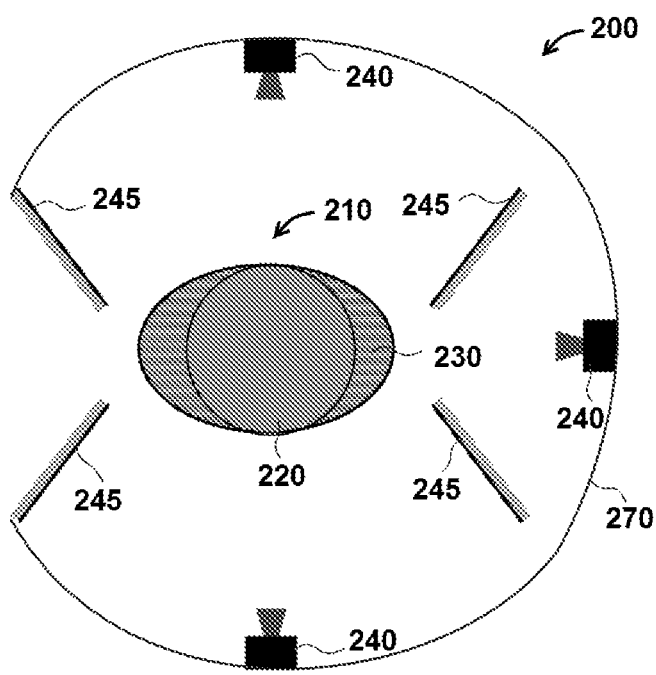
FIG. 2 shows a 3D detector system using a cylindrical plastic scintillator encased in an elliptic cylinder encasing body. Scintillation light is collected by a few CCD cameras. Mirrors are used to redirect light exiting the phantom at various angles toward the cameras.

FIG. 2 shows a 3-D detector system 200 using a cylindrical plastic scintillator assembly 210 comprising an active element 220 encased in an elliptic cylinder encasing body 230. In this embodiment, light is collected by a fewer number of light detectors 240, and mirrors are used to redirect light exiting body 230 at various angles toward light detectors 240. This embodiment is generally equivalent to the embodiment shown in FIG. 1, except that a smaller number of light detectors 240 is used (FIG. 2 shows three detectors), and the number of viewing angles is increased by using mirrors 245 to redirect light from areas that would otherwise not be measured by light detectors 240. In this embodiment, mirrors are enclosed in housing 270. Light detectors 240 are directed so that part of the detected image is formed by light traveling directly from active element 220, while another section of the same image is formed by light traveling from a different direction and redirected by a mirror 245.

In the embodiment shown in FIG. 2, the reconstruction algorithm is the same as in the first embodiment, except that each image is segmented into the direct and reflected image, and the reflected image is projected from the appropriate direction in the reconstruction algorithm.

Figure 3:
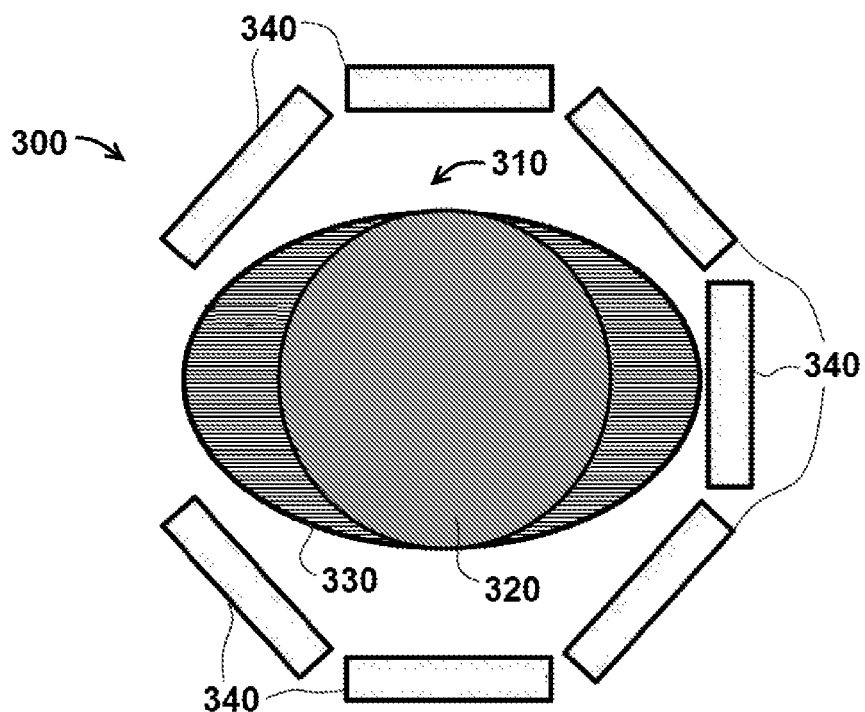
FIG. 3 shows a 3D detector system using a cylindrical plastic scintillator encased into an elliptic cylinder encasing body. Scintillation light is collected by arrays of photodetectors. A gap is left to allow for delivery of the radiation beam.

FIG. 3 shows a 3D detector system 300 using a cylindrical plastic scintillator assembly 310 comprising an active element 320 encased into an elliptic cylinder encasing body 330. This detector system is similar to that described in the embodiment of FIG. 1, except that the light detectors are specifically configured as arrays of photodetectors 340, including for example, photodiodes. Photodetector arrays 340 may be positioned in the same locations as the light detectors 140 in the embodiment of FIG. 1, with or without collimators. Additionally, photodetector arrays 340 may be attached directly to the surface of the encasing body 330 or to a collimator on the surface of encasing body 330. Such a design can provide a more compact device and decrease artifacts caused by refraction.

Figure 4:
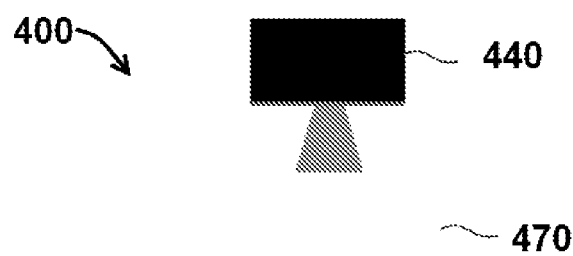
FIG. 4 shows a 3D detector system using a cylindrical plastic scintillator with no encasing body. This embodiment utilizes a single CCD camera, which is attached to a track surrounding the cylindrical surface of the plastic scintillator. The housing may be moved along the track by means of a motor, allowing the camera to view the detector from multiple angles.
Figure 4:
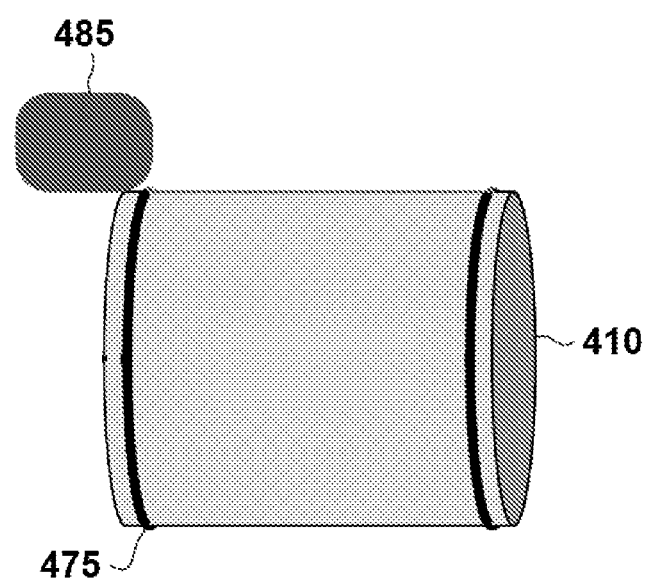

FIG. 4 shows a 3-D detector system 400 using a cylindrical plastic scintillator 410. In this embodiment, there is no encasing body and scintillator 410 is expanded to comprise the entire bulk of the 'phantom' component of the detector. In this embodiment, the entire phantom is the active volume, and radiation dose measurements may be acquired throughout the entire phantom volume.

This embodiment utilizes a light detector 440 coupled to a housing 470, which is in turn coupled to a track 475 surrounding the cylindrical surface of a plastic scintillator 410. In certain embodiments, light detector 440 may be configured as a single CCD camera. Housing 470 may be moved along track 475 by means of a motor 485. This can allow light detector 440 to view scintillator 410 from multiple angles.

The operation of this embodiment is similar to the embodiment of FIG. 1, but instead of acquiring images from multiple images simultaneously through multiple detectors, images can be acquired sequentially, with motor 485 moving light detector 440 to a different position for each image. By repeating the dose delivery at several light detector positions, a 3-D map of the radiation dose can be reconstructed using only one light detector 440.

Figure 5:
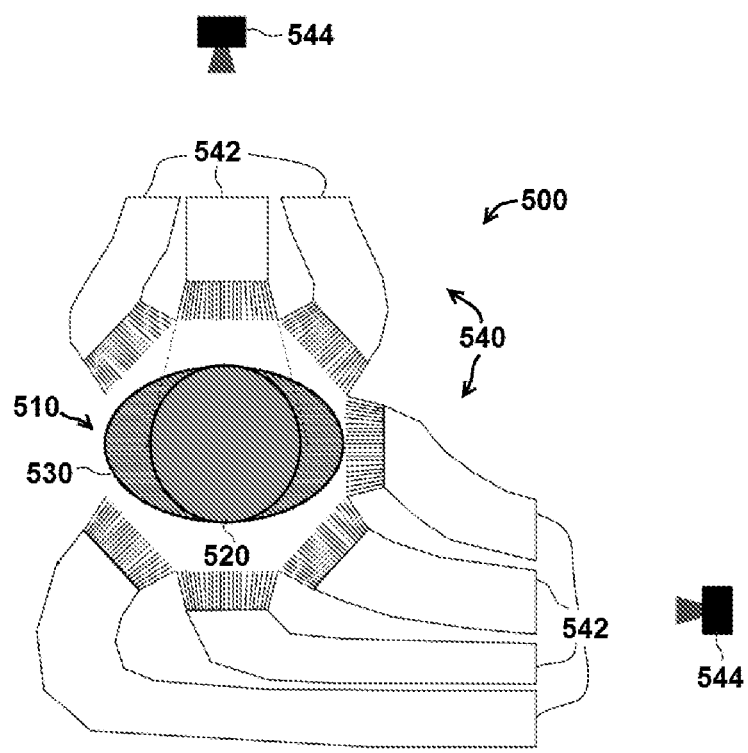
FIG. 5 shows a 3D detector system using a cylindrical plastic scintillator encased in an elliptical encasing body. Light is collected by bundles of optical fibers with low numerical aperture. The optical fibers are then directed toward photo-detectors such as CCD cameras.

FIG. 5 shows a 3-D detector system 500 using a cylindrical plastic scintillator assembly 510 comprising an active element 520 encased in an elliptical encasing body 530. In this embodiment, light can be collected by light detectors 540 configured as bundles of optical fibers 542 directed toward photo-detectors 544 (e.g. CCD cameras), where the light signals are recorded. In particular embodiments, optical fibers 542 have a low numerical aperture. The 3-D light emission reconstruction can be accomplished by mapping the signal from each optical fiber 542 to its location on encasing body 530 and using an iterative or backprojection algorithm to reconstruct the 3-D light emission.

Figure 6:
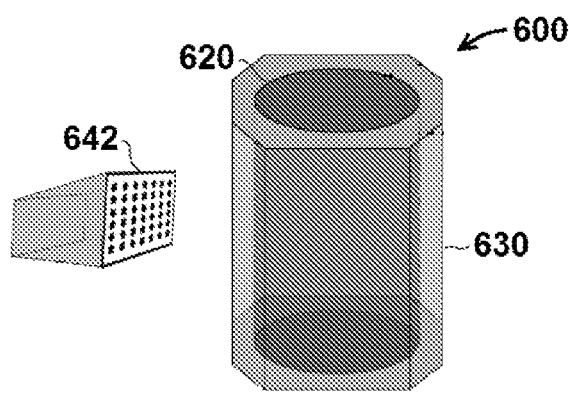
FIG. 6 shows a 3D representation of a detector system using a fiber optic bundle. Only a single fiber optic bundle is shown for clarity. In this case, a cylindrical scintillator sensitive volume is encased in an octagonal phantom (encasing body).

FIG. 6 shows a schematic perspective view of a detector system 600 comprising a fiber optic bundle 642. In the embodiment shown in FIG. 6, only a single fiber optic bundle 642 is shown for clarity. It is understood that exemplary embodiments may comprise multiple fiber optic bundles. In this embodiment, a cylindrical scintillator sensitive volume 620 is encased in an octagonal phantom 630. The use of an encasing body with flat faces can simplify the construction process.

Figure 7:
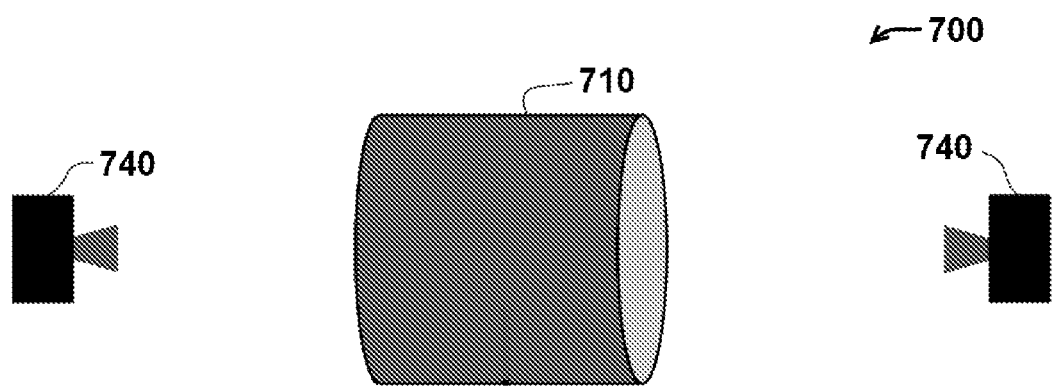
FIG. 7 shows a 3D detector system using a cylindrical plastic scintillator with no encasing body. Light is collected by one or two light field cameras facing the flat ends of the cylindrical plastic scintillator.

FIG. 7 shows a 3-D detector system 700 using a cylindrical plastic scintillator 710 with no encasing body. In this embodiment, light can be collected by one or two light detectors 740 (including for example, light field cameras) facing the flat ends of the cylindrical plastic scintillator 710. In certain embodiments, light field cameras can measure the intensity and direction of incoming light rays, making it possible to recover depth information from a single camera image and to refocus the image after it has been acquired. The 3-D reconstruction process in this embodiment may involve the refocusing of the image at multiple distances to obtain a slice of the light distribution at each focal depth. Reconstruction may also be performed by projecting the light intensity and direction back through the scintillator volume for each measured light ray.

Figure 8:
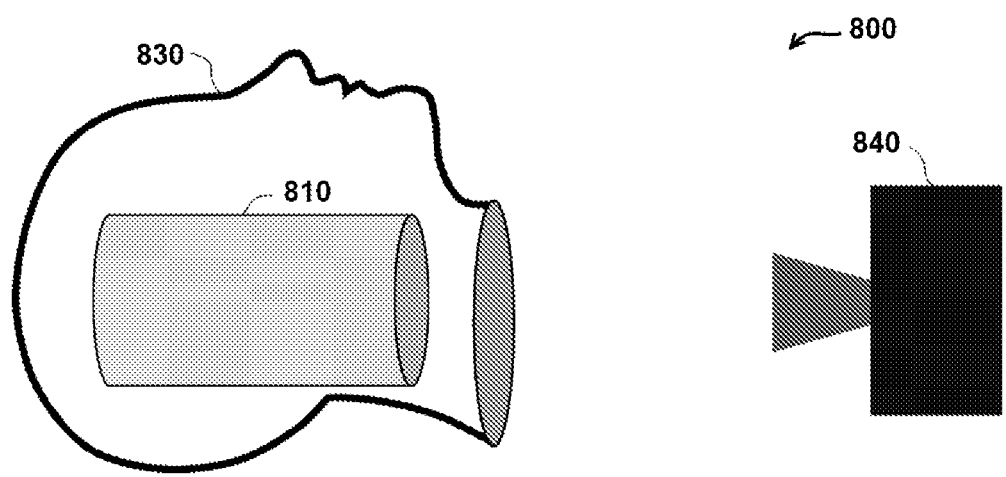
FIG. 8 shows a 3D detector system using a cylindrical plastic scintillator inside an encasing body in the shape of a part of the human anatomy. Light is collected by a light field camera facing a flat face of the encasing body.

FIG. 8 shows a 3-D detector system 800 using a cylindrical plastic scintillator 810 inside an encasing body 830 in the shape of a part of the human anatomy. In particular embodiments, scintillator 810 may be fixed or removable. Scintillation light can be collected by a light detector 840 (including for example, a light field camera) facing a flat face of encasing body 830. In certain embodiments, additional light detectors may be added. In particular embodiments, light refractions caused by a curved surface of the encasing body may be corrected by applying an angle-dependent refraction calculation to the detected images or by flattening the surface of the encasing body where it is viewed by each light detector 840.

Figure 9:
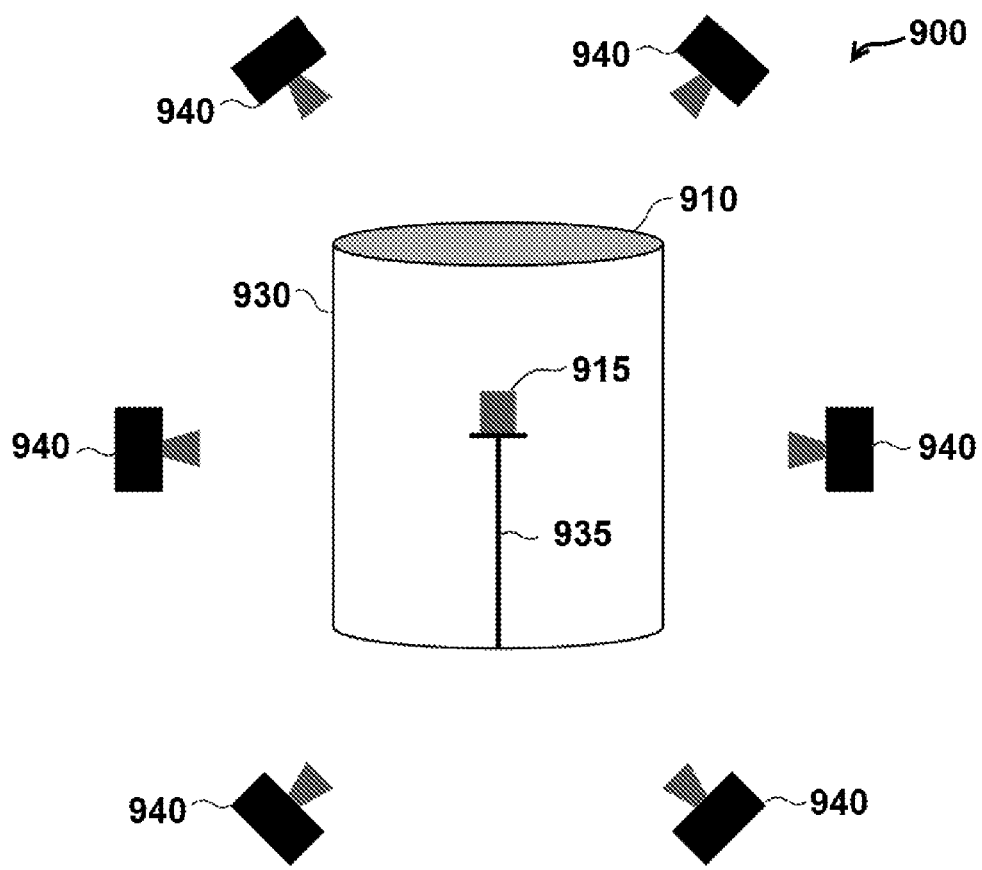
FIG. 9 shows a 3D detector system using a transparent cylindrical tank filled with liquid or gelatinous scintillator material. A stand is provided within the tank for the placement of radioactive sources. The tank is surrounded by CCD cameras.

FIG. 9 shows a 3-D detector system 900 using a cylindrical tank 930 filled with liquid or gelatinous scintillator material 910. In the embodiment shown, a stand 935 is provided within tank 930 for the placement of a radioactive source 915. Tank 930 can be surrounded by light detectors 940 (including for example, CCD cameras). In certain embodiments, the 3-D radiation dose distribution from source 915 can be measured by placing source 915 on stand 935 and measuring the light emission from multiple angles using light detectors 940. In particular embodiments, the dose distribution can be reconstructed from the detected images using filtered backprojection or iterative reconstruction algorithms.

Figure 10:
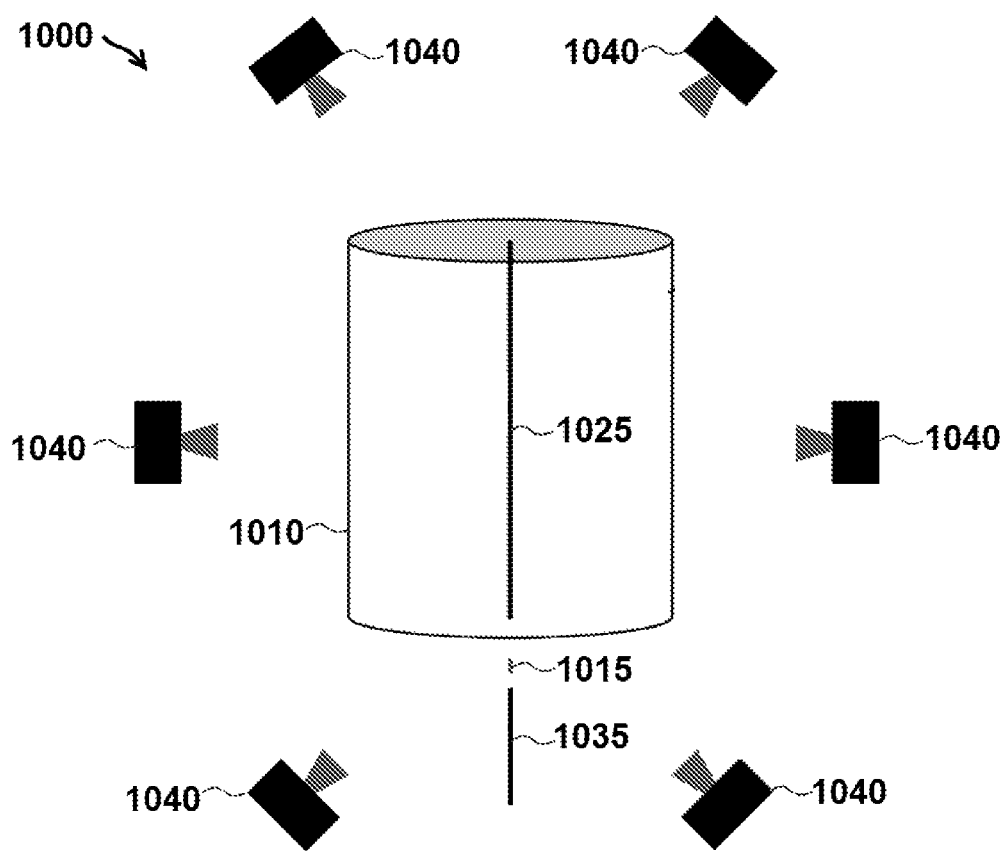
FIG. 10 shows a 3D detector system using a cylindrical plastic scintillator with no encasing body. A hole is drilled through the center of the tank, whereby a radioactive source can be positioned in the center of the cylindrical plastic scintillator with a support rod. The scintillator is surrounded by CCD cameras.

FIG. 10 shows a 3-D detector system 1000 using a cylindrical plastic scintillator 1010 with no encasing body. In the embodiment shown, a channel 1025 is drilled through the center of scintillator 1010, whereby a radioactive source 1015 can be positioned in the center of cylindrical plastic scintillator 1010 with a support rod 1035. In particular embodiments, channel 1025 may extend through the entire scintillator block 1010 or channel 1025 may extend halfway through. In particular embodiments, the width of channel 1025 can correspond to the width of radioactive source 1015 to be measured. In certain embodiments, the width of channel 1025 can be slightly larger than a catheter used with a high-dose-rate brachytherapy robotic afterloader. Scintillator 1010 can be surrounded by light detectors 1040 (including for example, CCD cameras). In certain embodiments, radioactive source 1015 can placed in channel 1025 either using a catheter and robotic afterloader or by placing the source inside the hole and positioning it with a support rod 1022. In particular embodiments, the dose distribution can be reconstructed from detected images using filtered backprojection or iterative reconstruction algorithms.

Additional embodiments may comprise a circular tank filled with a scintillating liquid or circular solid scintillating embodiment of any dimension. Such a structure could have a one CCD, CMOS, light field camera or any type of photodetector or detector system capturing the light produced from the circular lateral surface of such tank or embodiment. The entire apparatus can be stationary or mounted on a motor that would rotate the entire assembly at a continuous rate or to discrete positions.

All of the devices, systems and/or methods disclosed and claimed herein can be made and executed without undue experimentation in light of the present disclosure. While the devices, systems and methods of this invention have been described in terms of particular embodiments, it will be apparent to those of skill in the art that variations may be applied to the devices, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The contents of the following references are incorporated by reference herein:
U.S. Pat. No. 7,804,075
U.S. Pat. No. 7,432,510
U.S. Pat. No. 7,154,097
U.S. Pat. No. 6,125,335
U.S. Pat. No. 6,087,666
U.S. Pat. No. 6,066,851
U.S. Pat. No. 5,905,263
U.S. Pat. No. 5,856,673
U.S. Pat. No. 5,265,475
U.S. Pat. No. 8,183,534
U.S. Patent Pub. 20090014665
U.S. Patent Pub. 20060027756
U.S. Patent Pub. 20060017009
U.S. Patent Pub. 20120068075
U.S. Patent Pub. 20120168630
U.S. Patent Pub. 20090236510
U.S. Patent Pub. 20100001189
U.S. Patent Pub. 20080272310
U.S. Patent Pub. 20070057164
U.S. Patent Pub. 20080169421
U.S. Patent Pub. 20060169917
U.S. Patent Pub. 20020125412
U.S. Patent Pub. 20090294687
U.S. Patent Pub. 20080073568
U.S. Patent Pub. 20010047136
U.S. Patent Pub. 20050195318

The invention claimed is:

1. A radiation dose detector device, comprising:
a scintillating element;
a plurality of light detectors configured to detect light emitted from the scintillating element, wherein:
the plurality of light detectors are coupled to a housing extending around the scintillating element;
each light detector of the plurality of light detectors comprises a field of view;
the entire scintillating element is in the field of view of each light detector of the plurality of light detectors; and
a computer, wherein the computer is configured to receive data from the plurality of light detectors and configured to generate a three-dimensional map of light emitted from the scintillating element.

2. The radiation dose detector device of claim 1 wherein the plurality of light detectors are configured to simultaneously detect light emitted from the scintillating element.

3. The radiation dose detector device of claim 1 wherein at least one of the plurality of light detectors are selected from the group consisting of: charge-coupled device (CCD) cameras, complementary metal-oxide sensor (CMOS) cameras, light field cameras, photodiode arrays and photomultiplier tube arrays.

4. The radiation dose detector device of claim 1 wherein the plurality of light detectors are coupled to a housing, wherein the housing is configured to block external light from entering the radiation dose detector.

5. The radiation dose detector device of claim 1 further comprising a collimator between the scintillating element and at least one of the plurality of light detectors.

6. The radiation dose detector device of claim 1 further comprising one or more optical fibers between the scintillating element and at least one of the plurality of light detectors.

7. The radiation dose detector device of claim 1 wherein the computer comprises a computer readable medium comprising software configured to execute a pre-processing algorithm, a tomographic reconstruction algorithm and a post-processing algorithm.

8. The radiation dose detector device of claim 7 wherein the pre-processing algorithm is configured to correct for both optical and dosimetric artifacts.

9. The radiation dose detector device of claim 7 wherein the tomographic reconstruction algorithm converts data received from the plurality of light detectors into a three-dimensional dose distribution.

10. The radiation dose detector device of claim 9 wherein the tomographic reconstruction algorithm comprises a filtered backprojection algorithm.

11. The radiation dose detector device of claim 9 wherein the tomographic reconstruction algorithm comprises an iterative algorithm.

12. The radiation dose detector device of claim 7 wherein the post-processing algorithm is configured to convert grayscale levels of three-dimensional light distribution into actual dose values by comparison with a reference measurement.

13. A three-dimensional radiation dose detector device, comprising:
a continuous volumetric scintillating element; and
means for measuring the light emission from said scintillating element from multiple positions or directions simultaneously and with high temporal resolution, wherein:
said means for measuring the light emission from said scintillating element is positioned around said scintillating element;
said means for measuring the light emission from said scintillating element comprises a depth of field that extends through said scintillating element.

14. The radiation dose detector device of claim 13 wherein the continuous volumetric scintillating element has a volume of about 500 to 15,000 cubic centimeters.

15. The radiation dose detector device of claim 13 wherein the temporal resolution is up to 100 samples per second.

16. The radiation dose detector device of claim 13, wherein said scintillating element is an organic or inorganic material in solid, liquid, or gelatinous state.

17. The radiation dose detector device of claim 13, wherein said means for measuring light emission comprises one or more charge-coupled devices, complementary metal-oxide-semiconductor devices, light field cameras, photomultiplier tubes, photodiodes, avalanche photodiodes.

18. The radiation dose detector device of claim 13, wherein said means of measuring light emission comprises one or more light-field imagers or plenoptic cameras.

19. The radiation dose detector of claim 13, wherein said means for measuring light emission includes detectors equally spaced at an angle $\theta$, with the sum of all angles equal to 360 degrees.

20. The radiation dose detector device of claim 13, wherein said means for measuring light emission includes detectors unequally-spaced at angles $\theta i$, where the sum of all $\theta i$ equals 360 degrees or less.

* * * * *